(12) United States Patent
Madonna et al.

(10) Patent No.: US 9,394,343 B2
(45) Date of Patent: Jul. 19, 2016

(54) APPETITE STIMULATING PROTEIN

(75) Inventors: Michael Madonna, Santa Cruz, CA (US); Stephen Benoit, Cincinnati, OH (US); Glenn Millhauser, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/130,916

(22) PCT Filed: Jul. 4, 2012

(86) PCT No.: PCT/US2012/045474
§ 371 (c)(1),
(2), (4) Date: Jan. 4, 2014

(87) PCT Pub. No.: WO2013/006656
PCT Pub. Date: Jan. 10, 2013

(65) Prior Publication Data
US 2014/0148397 A1     May 29, 2014

Related U.S. Application Data

(60) Provisional application No. 61/504,370, filed on Jul. 5, 2011.

(51) Int. Cl.
*A61K 38/00* (2006.01)
*C07K 16/00* (2006.01)
*C07K 14/00* (2006.01)
*C07K 14/47* (2006.01)

(52) U.S. Cl.
CPC ............... *C07K 14/00* (2013.01); *C07K 14/47* (2013.01)

(58) Field of Classification Search
None
See application file for complete search history.

(56) References Cited

U.S. PATENT DOCUMENTS

2005/0282739 A1* 12/2005 Sharma et al. ............ 514/6
2010/0260706 A1   10/2010   Bogin

FOREIGN PATENT DOCUMENTS

EP    1125579    8/2001
JP    8165302    6/1996

OTHER PUBLICATIONS

Madonna et. al. Feb. 2012,ACS Chem. Biol. 17; 7(2): 395-402. doi: 10.1021/cb2003412.*
Madonna et al. ACS Chem Biol 2013 vol. 7 No. 2 395-402 published on line Nov. 30, 2011 pp. 1-18 esp. abstract pp. 1,2, 2 and table 1.

* cited by examiner

*Primary Examiner* — Jeanette Lieb
(74) *Attorney, Agent, or Firm* — Adam Warwick Bell; Matthew Rupert Kaser

(57) ABSTRACT

An engineered polypeptide comprising an AgRP analog with increased basic residues compared to the wild type polypeptide, wherein the polypeptide, when introduced into the CNS of a mammal, stimulates appetite.

8 Claims, 7 Drawing Sheets

APPETITE STIMULATING PROTEIN

RELATIONSHIP TO OTHER APPLICATIONS

This application is a US National phase application of PCT/US12/45474 filed 4 Jul. 2012 and claims priority to and the benefit of U.S. provisional application No. 61/504,370 filed 5 Jul. 2011, each of which is fully incorporated by reference.

GOVERNMENT SUPPORT CLAUSE

This invention was made with support of National Institutes of Health grant No. DK064265; the government has certain rights in the invention.

FIELD OF THE INVENTION

The invention relates to the stimulation of appetite, and to molecules that stimulate appetite, specifically, the invention relates to elements within the Agouti-Related Protein (AgRP) which elements are positioned outside of the Receptor Binding Core and have been found to enhance short and long term feeding in mammals.

BACKGROUND OF THE INVENTION

The Agouti-Related Protein (AgRP) plays a central role in energy balance by reducing signaling through the hypothalamic melanocortin receptors (MCRs) 3 and 4, in turn stimulating feeding and decreasing energy expenditure. The inventors have examined the functions of the N-terminal extension and a C-terminal loop of AgRP in controlling appetite. The present study suggests new strategies for the development of potent orexigenic species, and treating wasting conditions such as cachexia.

SUMMARY OF THE INVENTION

The data described provides unexpectedly superior results when the polypeptides of the invention are used as an appetite stimulant. The invention encompasses polypeptides and synthetic, engineered, non-naturally occurring analogues of the AgRP protein and methods for creating and using such polypeptides and analogues.

The invention encompasses compositions and isolated and/or engineered non-naturally occurring constructs including polypeptides comprising elements related to and/or derived from sequences within the Agouti-Related Protein (AgRP) which elements are positioned outside of the Receptor Binding Core and have been found to enhance short and long term feeding in mammals.

The invention encompasses uses for such engineered non-naturally occurring constructs comprising polypeptides that include elements related to and/or derived from sequences within the Agouti-Related Protein (AgRP).

In one embodiment the invention encompasses a polypeptide comprising an AgRP (83-132) analog with increased positive charge compared to the wild type polypeptide, wherein the polypeptide, when introduced into the CNS of a mammal, stimulates appetite. This polypeptide, when introduced into the CNS of a mammal, stimulates appetite and results in enhanced feeding that is measurably at least double that obtained when unaltered AgRP (83-132) is introduced into the CNS of a mammal.

In one embodiment the invention encompasses a polypeptide comprising an engineered, non-naturally occurring amino acid sequence selected from the following polypeptide sequences:

| SEQ ID No. | Name | N-term | Inhibitor Cystine Knot Core | C-Term Loop |
|---|---|---|---|---|
| SEQ ID No. 1 | AgRP(83-120) | SSRR | CVRLHESCLGQQVPCCDPAATCYCRFFNAFCYC | R |
| SEQ ID No. 2 | AgRP(87-132) | | CVRLHESCLGQQVPCCDPCATCYCRFFNAFCYC | RKLGTAMNPCSRT |
| SEQ ID No. 3 | AgRP(87-120) | | CVRLHESCLGQQVPCCDPAATCYCRFFNAFCYC | R |
| SEQ ID No. 4 | AgRP-2Q | SSRR | CVRLHESCLGQQVPCCDPCATCYCRFFNAFCYC | RQLGTAMNPCSQT |
| SEQ ID No. 5 | AgRP-4Q | SSQQ | CVRLHESCLGQQVPCCDPCATCYCRFFNAFCYC | RQLGTAMNPCSQT |
| SEQ ID No. 6 | AgRP-2K | SSRR | CVRLHESCLGQQVPCCDPCATCYCRFFNAFCYC | RKLKTKMNPCSRT |
| SEQ ID No. 7 | AgRP-4K | KKRR | CVRLHESCLGQQVPCCDPCATCYCRFFNAFCYC | RKLKTKMNPCSRT |

In certain embodiments, the polypeptide is an engineered polypeptide comprising a non-naturally occurring amino acid sequence having a specific degree of polypeptide sequence identity to a polypeptide sequence disclosed above, such as, for example, 60%, 65%, 70%, 75%, 85%, 90%, 95%, 99% or 100% sequence identity to a polypeptide sequence disclosed.

In certain embodiments, the non-naturally occurring amino acid sequence may have other amino acid changes (deletions, additions or substitutions) apart from those provided above. In certain embodiments, these other amino acid changes may increase the overall basic nature of the polypeptide.

In other embodiments the non-naturally occurring amino acid sequence may include other conservative amino acid substitutions apart from those provided above.

Further, the invention encompasses a method for increasing appetite or for treating cachexia, the method comprising administering to a subject a polypeptide described herein.

Additionally the invention encompasses a polynucleotide encoding an engineered, non-naturally occurring amino acid sequence selected from the amino acid sequences disclosed. Also encompassed are engineered expression vectors and other polynucleotide constructs encoding any of the disclosed engineered non-naturally occurring polypeptide constructs. Also encompassed are organisms comprising any of the disclosed engineered non-naturally occurring polypeptide constructs.

Also encompassed are methods for producing any of the disclosed engineered non-naturally occurring polypeptide constructs by transcription and translation of a polynucleotide encoding such polypeptides.

GENERAL DISCLOSURES AND DEFINITIONS

Figure 1:
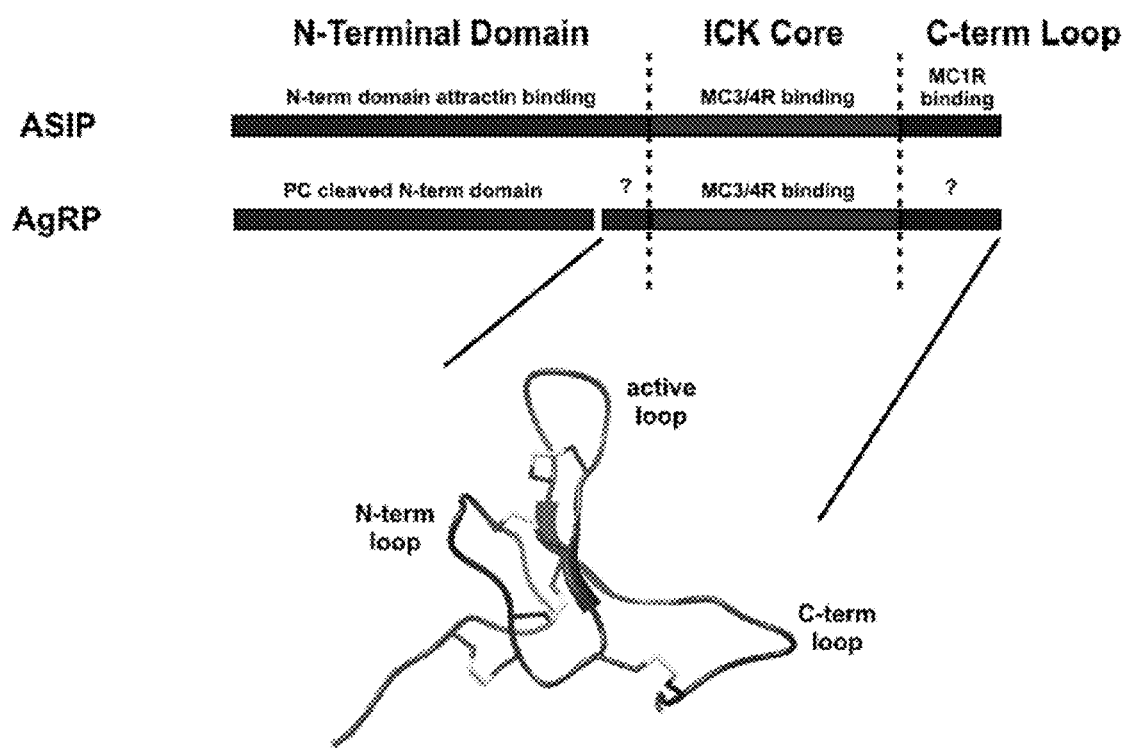
FIG. 1. Schematic of ASIP and AgRP structure/function. The sequence diagram illustrates homologous regions of the two proteins and corresponding functions. Question marks indicate the two regions of AgRP of unknown function. Structure of AgRP(83-132) illustrates the spatial location of the different regions.

In the disclosure, the terms "a" and "an" as used herein do not denote a limitation of quantity, but rather denote the presence of at least one of the referenced items. All publications mentioned herein are incorporated by reference for all purposes to the extent allowable by law.

The term "antisense" refers to any composition containing a nucleic acid sequence which is complementary to the "sense" strand of a specific nucleic acid sequence. Antisense molecules may be produced by any method including synthesis or transcription. Once introduced into a cell, the complementary nucleotides combine with natural sequences produced by the cell to form duplexes and to block either transcription or translation. The designation "negative" or "minus" can refer to the antisense strand, and the designation "positive" or "plus" can refer to the sense strand.

The terms "complementary" and "complementarity" refer to the natural binding of polynucleotides by base pairing. For example, the sequence "5' A-G-T 3'" bonds to the complementary sequence "3' T-C-A 5'." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands.

"Conservative amino acid substitutions" are those substitutions that, when made, least interfere with the properties of the original protein, i.e., the structure and especially the function of the protein is conserved and not significantly changed by such substitutions. The table below shows amino acids which may be substituted for an original amino acid in a protein and which are regarded as conservative amino acid substitutions.

| Original Residue | Conservative Substitution |
|---|---|
| Ala | Gly, Ser |
| Arg | His, Lys |
| Asn | Asp, Gln, His |
| Asp | Asn, Glu |
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Leu, Ile |
| Phe | His, Met, Leu, Trp, Tyr |
| Ser | Cys, Thr |
| Thr | Ser, Val |
| Trp | Phe, Tyr |
| Tyr | His, Phe, Trp |
| Val | Ile, Leu, Thr |

Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

The term "derivative" refers to the chemical modification of a polypeptide sequence, or a polynucleotide sequence. Chemical modifications of a polynucleotide sequence can include, for example, replacement of hydrogen by an alkyl, acyl, hydroxyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

A "fragment" is a unique portion of a parent sequence which is identical in sequence to but shorter in length than the parent sequence. A fragment may comprise up to the entire length of the defined sequence, minus one nucleotide/amino acid residue. For example, a fragment may be at least 5, 10, 15, 20, 25, 30, 40, 50, 60, 75, 100, 150, 250 or at least 500 contiguous nucleotides or amino acid residues in length. Fragments may be preferentially selected from certain regions of a molecule. For example, a polypeptide fragment may comprise a certain length of contiguous amino acids selected from the first 250 or 500 amino acids (or first 25% or 50% of a polypeptide) as shown in a certain defined sequence. Clearly these lengths are exemplary, and any length that is supported by the specification, including the Sequence Listing, tables, and figures, may be encompassed by the present embodiments.

The phrases "percent identity" and "% identity," as applied to polynucleotide sequences, refer to the percentage of residue matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences. Percent identity between polynucleotide sequences may be determined using the default parameters of the CLUSTAL V algorithm as incorporated into the MEGALIGN version 3.12e sequence alignment program. This program is part of the LASERGENE software package, a suite of molecular biological analysis programs (DNASTAR, Madison Wis.). CLUSTAL V is described in Higgins, D. G. and P. M. Sharp (1989) CABIOS 5:151-153 and in Higgins, D. G. et al. (1992) CABIOS 8:189-191. For pairwise alignments of polynucleotide sequences, the default parameters are set as follows: Ktuple=2, gap penalty=5, window=4, and "diagonals saved"=4. The "weighted" residue weight table is selected as the default. Percent identity is reported by CLUSTAL V as the "percent similarity" between aligned polynucleotide sequence pairs. Alternatively, a suite of commonly used and freely available sequence comparison algorithms is provided by the National Center for Biotechnology Information (NCBI) Basic Local Alignment Search Tool (BLAST) (Altschul, S. F. et al. (1990) J. Mol. Biol. 215:403-410). The "BLAST 2 Sequences" tool can be used for both blastn and blastp (discussed below). BLAST programs are commonly used with gap and other parameters set to default settings. For example, to compare two nucleotide sequences, one may use blastn with the "BLAST 2 Sequences" tool Version 2.0.9 (May 7, 1999) set at default parameters. Such default parameters may be, for example: Matrix: BLOSUM62; Reward for match: 1; Penalty for mismatch: −2; Open Gap: 5 and Extension Gap: 2 penalties; Gap x drop-off: 50; Expect: 10; Word Size: 11; .Filter: on.

Percent identity may be measured over the length of an entire defined sequence, for example, as defined by a particular SEQ ID number, or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length supported by the sequences shown herein, in the tables, figures, or Sequence Listing, may be used to describe a length over which percentage identity may be measured.

The phrases "percent identity" and "% identity," as applied to polypeptide sequences, refer to the percentage of residue matches between at least two polypeptide sequences aligned using a standardized algorithm. Methods of polypeptide sequence alignment are well-known. Some alignment methods take into account conservative amino acid substitutions. Such conservative substitutions, explained in more detail above, generally preserve the hydrophobicity and acidity at the site of substitution, thus preserving the structure (and therefore function) of the polypeptide.

Percent identity between polypeptide sequences may be determined using the default parameters of the CLUSTAL V algorithm as incorporated into the MEGALIGN version 3.12e sequence alignment program (described and referenced above). For pairwise alignments of polypeptide sequences using CLUSTAL V, the default parameters are set as follows: Ktuple=1, gap penalty=3, window=5, and "diagonals saved"=5. Percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

"Hybridization" refers to the process by which a polynucleotide strand anneals with a complementary strand through base pairing under defined hybridization conditions. Specific hybridization is an indication that two nucleic acid sequences share a high degree of identity. Specific hybridization complexes form under permissive annealing conditions and remain hybridized after the "washing" step(s). The washing step(s) is particularly important in determining the stringency of the hybridization process, with more stringent conditions allowing less non-specific binding, i.e., binding between pairs of nucleic acid strands that are not perfectly matched. Permissive conditions for annealing of nucleic acid sequences are routinely determinable by one of ordinary skill in the art and may be consistent among hybridization experiments, whereas wash conditions may be varied among experiments to achieve the desired stringency, and therefore hybridization specificity. Permissive annealing conditions occur, for example, at 68° C. in the presence of about 6×SSC, about 1% (w/v) SDS, and about 100 µg/ml denatured salmon sperm DNA. Generally, stringency of hybridization is expressed, in part, with reference to the temperature under which the wash step is carried out. Generally, such wash temperatures are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. An equation for calculating $T_m$ and conditions for nucleic acid hybridization are well known and can be found in Sambrook et al., 1989, Molecular Cloning: A Laboratory Manual, $2^{nd}$ ed., vol. 1-3, Cold Spring Harbor Press, Plainview N.Y.; specifically see volume 2, chapter 9. High stringency conditions for hybridization between polynucleotides of the present invention include wash conditions of 68° C. in the presence of about 0.2×SSC and about 0.1% SDS, for 1 hour. Alternatively, temperatures of about 65° C., 60° C., 55° C., or 42° C. may be used. SSC concentration may be varied from about 0.1 to 2×SSC, with SDS being present at about 0.1%. Typically, blocking reagents are used to block non-specific hybridization. Such blocking reagents include, for instance, denatured salmon sperm DNA at about 100-200 µg/ml. Organic solvent, such as formamide at a concentration of about 35-50% v/v, may also be used under particular circumstances, such as for RNA:DNA hybridizations. Useful variations on these wash conditions will be readily apparent to those of ordinary skill in the art. Hybridization, particularly under high stringency conditions, may be suggestive of evolutionary similarity between the nucleotides. Such similarity is strongly indicative of a similar role for the nucleotides and their encoded polypeptides.

The phrases "nucleic acid" and "nucleic acid sequence" refer to a nucleotide, oligonucleotide, polynucleotide, or any fragment thereof. These phrases also refer to DNA or RNA of genomic or synthetic origin which may be single-stranded or double-stranded and may represent the sense or the antisense strand, to peptide nucleic acid (PNA), or to any DNA-like or RNA-like material.

"Operably linked" refers to the situation in which a first nucleic acid sequence is placed in a functional relationship with the second nucleic acid sequence. For instance, a promoter is operably linked to a coding sequence if the promoter affects the transcription or expression of the coding sequence. Generally, operably linked DNA sequences may be in close proximity or contiguous and, where necessary to join two protein coding regions, in the same reading frame.

A "variant" of a particular nucleic acid sequence is defined as a nucleic acid sequence having at least 40% sequence identity to the particular nucleic acid sequence over a certain length of one of the nucleic acid sequences using blastn with the "BLAST 2 Sequences" tool Version 2.0.9 (May 7, 1999) set at default parameters. Such a pair of nucleic acids may show, for example, at least 50%, at least 60%, at least 70%, at least 80%, at least 85%, at least 90%, at least 95% or at least 98% or greater sequence identity over a certain defined length. A variant may be described as, for example, an "allelic" (as defined above), "splice," "species," or "polymorphic" variant. A splice variant may have significant identity to a reference molecule, but will generally have a greater or lesser number of polynucleotides due to alternate splicing of exons during mRNA processing. The corresponding polypeptide may possess additional functional domains or lack domains that are present in the reference molecule. Species variants are polynucleotide sequences that vary from one species to another. The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs) in which the polynucleotide sequence varies by one nucleotide base. The presence of SNPs may be indicative of, for example, a certain population, a disease state, or a propensity for a disease state.

A "variant" of a particular polypeptide sequence is defined as a polypeptide sequence having at least 40% sequence identity to the particular polypeptide sequence over a certain length of one of the polypeptide sequences using blastp with the "BLAST 2 Sequences" tool Version 2.0.9 (May 7, 1999) set at default parameters. Such a pair of polypeptides may show, for example, at least 50%, at least 60%, at least 70%, at least 80%, at least 90%, at least 95%, or at least 98% or greater sequence identity over a certain defined length of one of the polypeptides.

The term "analog" as used herein encompasses variants and derivatives.

The term "non-naturally occurring" as used herein means not commonly found in nature and may be used to refer to a polynucleotide or polypeptide sequence that is synthesized or mutated to provide a sequence different from the standard wild-type sequence.

The term "engineered" as used herein to refer to a polypeptide or polynucleotide sequence means that all or some of the sequence has been either synthesized by man chemically or has been altered, for example by addition, deletion or substitution, to provide a desired sequence.

The term "designed" as used herein to refer to a polypeptide or polynucleotide sequence, for example a "designed AgRP sequence", means a sequence that has been intentionally altered or synthesized to produce a non-naturally occurring sequence.

DETAILED DESCRIPTION OF THE INVENTION

The invention relates to the stimulation of appetite. In particular the inventors have identified a number of synthetic proteins, motifs, epitopes, variants, derivatives and analogues of such proteins that encourage the stimulation of appetite when introduced into a mammal.

Specifically, the invention relates to elements within the Agouti-Related Protein (AgRP) which elements are positioned outside of the Receptor Binding Core and have been found to enhance short and long term feeding in mammals. The Agouti-Related Protein (AgRP) plays a central role in energy balance by reducing signaling through the hypothalamic melanocortin receptors (MCRs) 3 and 4, in turn stimulating feeding and decreasing energy expenditure. Mature AgRP produced by endoproteolytic processing, contains a central region that folds as an inhibitor cystine knot (ICK) stabilized by a network of disulfide bonds; this domain alone carries the molecular features for high affinity MCR binding and inverse agonism. Outside of the ICK domain are two polypeptide segments—an N-terminal extension and a C-terminal loop—both completely conserved but of unknown function. The inventors have investigated the physiological roles of these non-ICK segments by developing a panel of modified AgRPs that were administered to rats through intracerebroventricular (ICV) injection.

Analysis of food consumption demonstrates that basic (positively charged) residues are essential for potent short and long term AgRP stimulated feeding. Moreover, the inventors demonstrate an approximate linear relationship between protein charge density and 24 hour food uptake.

Next, the inventors developed artificial AgRP(83-132) analogs with increased positive charge and found that these species were substantially more potent than wild type. A single dose of one protein, designated AgRP-4K, results in enhanced feeding for well over a week and weight gain that is nearly double that of AgRP(83-132). These studies suggest new strategies for the development of potent orexigenic species, and may serve as leads for the development of therapeutics for treating wasting conditions such as cachexia and eating conditions such as anorexia.

The functions of the polypeptide segments outside of AgRP's ICK core are unknown (FIG. 1). The four residue segment preceding the ICK core (Ser-Ser-Arg-Arg) and the 13 residue C-terminal loop are both highly conserved among mammals (Table 1), yet deletion of these segments has absolutely no effect on the Mc3R or Mc4R binding affinities or in vitro activity.

To address the functional significance of the segments outside of the ICK core domain in mature AgRP(83-132) (FIG. 1), the inventors performed ICV experiments on Long-Evans rats using a panel of AgRP variants in which select non-ICK components are deleted.

The inventors find a remarkable relationship between long term feeding enhancement and net AgRP positive charge, carried mainly by the non-ICK segments.

The inventors have developed a series of novel AgRP constructs where charge is selectively varied. ICV experiments with these constructs not only supports the charge-feeding relationship, but also lead to the discovery of an AgRP analog that significantly increases initial and long term feeding relative to the wild type protein. Together, these studies demonstrate a critical physiological role for the non-ICK AgRP segments, and suggest new strategies in the development of reagents for treating cachexia and other conditions associated with negative energy balance.

Figure 2:
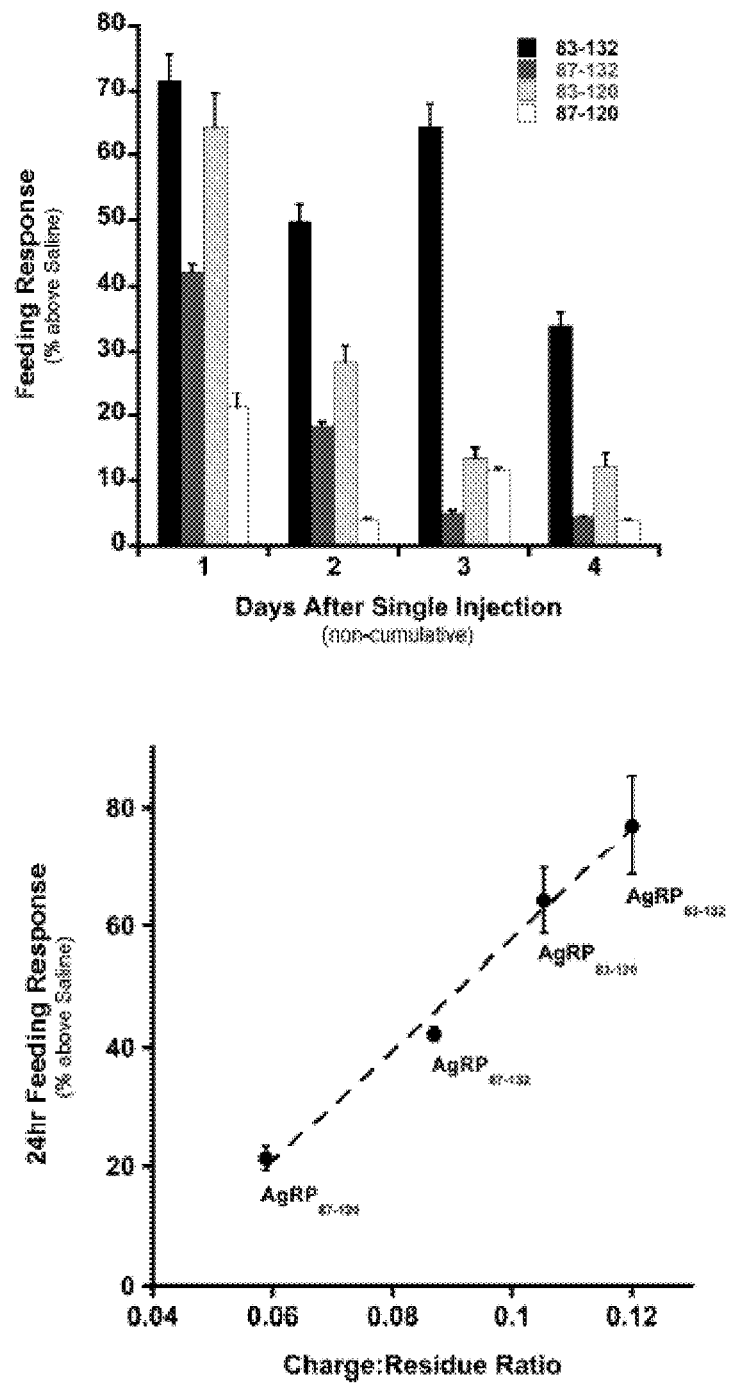
FIG. 2. Effect of a single third cerebral ventricle injection of 1.0 nmol AgRP proteins on male Long-Evans rats. (A) Percent increase over saline at 24 hr, 48 hr, 72 hr and 96 hr after injection (non-cumulative). (B) Net charge density trend of 24 hr feeding response above saline control. ✦ $P<0.001$, ‡ $P<0.01$, and * $P<0.05$.

The data in FIG. 2a suggest that (1) the four residue non-ICK segment preceding the ICK core is required for rapidly stimulating feeding, whereas (2) both non-ICK segments are needed for long term effects. Interestingly, there is an approximate linear relationship between 24 hour feeding and charge per residue (total protein charge divided by the number of amino acids). See FIG. 2b, showing a near four-fold increase in feeding from a doubling of the protein charge density.

Materials & Methods

Experimental Procedures

Peptide Synthesis, Purification and Folding

All peptides were synthesized using Fmoc synthesis on an Applied Biosystems (Foster City, Calif.) 433A Peptide Synthesizer on a 0.25 mmol scale. Syntheses were monitored using the SynthAssist version 2.0 software package. All peptides were assembled on a Rink-amide-MBHA. Amino acids and resins were purchased through NovaBiochem. HBTU was obtained from Advanced Chemtech (Louisville, Ky.), and all other reagents were purchased from Sigma-Aldrich (St. Louis, Mo.). Fmoc deprotection was achieved using a 1% hexamethyleneimine (HMI) and 1% 1,8-Diazabicyclo [4.5.0]-undec-7-ene (DBU) solution in DMF. Deprotection was monitored by conductivity and continued until the conductivity level returned to the baseline, then synthesis continued. Deprotection times ranged from 2.5-7 minutes. Couplings used 4 equivalents Fmoc-amino acid in HBTU/DIEA for all amino acids except pre-activated Fmoc-Cys(trt)-OPfp. A 3-fold excess of Fmoc-Cys(trt)-OPfp was dissolved in 1.5 mL 0.5M HOAt/DMF with no DIEA for coupling. AgRP(87-132) and AgRP(87-120) were the N-terminal is acetylated by reacting with 0.5M acetic anhydride in DMF for 5 minutes. Fully synthesized peptide resins were split into 3 reaction vessels, washed with DCM and dried. A solution of 12 mL TFA containing 200 mL each of TIS/EDT/liquefied Phenol (as scavengers) was added to each reaction vessel of dry peptide resin and incubated for 1.5 h. The resin was filtered and washed with 1 mL TFA and the combined filtrate and wash was then added to 90 mL cold dry diethyl ether for precipitation. The precipitate was collected by centrifugation and the ether was discarded. The pellet was dissolved in 40 mL 1:1 $H_2O$:CAN (0.1% TFA) and lyophilized.

Both peptides were purified by RP-HPLC on Vydac (Hesperia, Calif.) preparative C18 columns. Fractions were collected and analyzed by ESI-MS on a Micromass (Wythenshawe, UK) ZMD mass spectrometer to confirm the correct molecular weight. In each case the major peak was found to be the peptide, and fractions, which contained the peptide as a major constituent, were combined and lyophilized.

Air oxidative folding of each peptide was accomplished by dissolving the unfolded peptide into folding buffer (2.0M GuHCl/0.1M Tris, 3 mM GSH, 400 M GSSG, pH 8) at a peptide concentration of 0.1 mg/mL) and stirring for 24-36 h. Folding was monitored for all peptides by RP-HPLC on a C18 analytical column, which revealed a single peak, in each case, for the folded material that was shifted to an earlier retention time than the fully reduced peptide. The folded product was purified by RP-HPLC on a C18 preparative column and its identity confirmed as the fully oxidized product by ESI-MS. Reinjecting a small sample of the purified peptide on an analytical RP-HPLC column assessed purity of the peptides. Sample purity was determined to be >90%. Quantitative analysis of the peptide concentrations was done by UV absorption.

Rodent Studies

Male Long Evans rats ~10-12 weeks and weighing 250-350 g were obtained from Harlan (Indianapolis, Ind.) and maintained in an AALAC accredited vivarium on a 12 to 12 hr light dark cycle. Animals were given ad libitum access to standard rodent chow and water. After a one week habituation period, all animals were deeply anesthetized with a 1-ml/kg dose of (0.22 g Ketamine/0.03 g Xylazine) and placed into a sterotaxic apparatus with the incisor bars set at +1.0. Subsequently, an indwelling cannula was lowered into the third ventricle using the following coordinates, AP=−2.2, ML=0, DV=−7.0. All animals were allowed to recover for two weeks during which time they regained their pre-surgical body weight. To verify cannula placement, angiotensin II (10 ng/μl) was injected into the third ventricle and water consumption was measured over a one hour period. To be included animals had to drink more than 7 ml. Animals were injected one hour prior to the beginning of their dark phase using a within subjects paradigm. In all experiments n>6.

Pharmacology

The HEK-293 cell line was used for hMC3R and hMC4R transfection. The cells transfected with receptor were cultured in DMEM medium containing 10% bovine fetal serum and HEPES. Cells at 80% confluence were washed twice, and the receptor constructs were transfected into cells using lipofectamine.

Binding Assays

Binding experiments were performed using the conditions previously described. Briefly, after removal of the media, cells were incubated with non-radioligand NDP-MSH or AGRP analogues from $10^{-10}$ to $10^{-6}$ M in 0.5 ml MEM containing 0.2% BSA and $1 \times 10^5$ cpm of $^{125}$I-NDP-MSH for one hour. The binding reactions were terminated by removing the media and washing the cells twice with MEM containing 0.2% BSA. The cells were then lysed with 0.2 N NaOH, and the radioactivity in the lysate was quantified in an analytical gamma counter (PerkinElmer, Shelton, Conn.). Nonspecific binding was determined by measuring the amount of $^{125}$I-label bound on the cells in the presence of excess $10^{-6}$ M unlabeled ligand. Specific binding was calculated by subtracting nonspecifically bound radioactivity from total bound radioactivity.

cAMP Assays

Cellular cAMP generation was measured using a competitive binding assay kit (TRK 432, Amersham, Arlington Heights, Ill.). Briefly, cell culture media was removed, and cells were incubated with 0.5 ml Earle's Balanced Salt Solution (EBSS), containing the melanocortin agonist NDP-MSH ($10^{-10}$-$10^{-6}$ M), for one hour at 37° C. in the presence of $10^{-3}$ M isobutylmethylxanthine. The reaction was stopped by adding ice-cold 100% ethanol (500 μl/well). The cAMP content was measured as previously described, according to instructions accompanying the assay kit (Yang et al., 1997).

Results

Truncated AgRP Variants

Initial ICV injection experiments focused on truncated forms of mature AgRP(83-132) (Table 1). The minimal construct AgRP(87-120) was designed and investigated in a previous study (Jackson et al., 2002). Briefly, this protein lacks both the four residue segment before the ICK domain, and the C-terminal loop. Simple elimination of the C-terminal loop leaves an uncompensated Cys residue at position 105. To avoid the formation of non-native disulfide bonds, residue 105 was mutated to Ala. In addition, Arg120 following the penultimate Cys was retained as it is part of the β-sheet. Our previous NMR work showed that AgRP(87-120), often referred to as mini-AgRP, folds 100% to a uniform product that retains the ICK structure of the parent protein (Jackson et al., 2002). Moreover, dissociation constants measured at Mc3R and Mc4R are equivalent to mature AgRP(83-132). Two other constructs, AgRP(83-120) and AgRP(87-132) were prepared using the same strategies.

TABLE 1

Agouti Related Protein Sequences

| | N-term | Inhibitor Cystine Knot Core | C-Term Loop | SEQ ID No. |
|---|---|---|---|---|
| Human (83-132) | SS<u>RR</u> | CVRLHESCLGQQVPCCDPCATCYCRFFNAFCYC | <u>R</u>K<u>L</u>GTAMNPCS<u>R</u>T | SEQ ID No. 8 |
| Cow | SP<u>RR</u> | CVRLHESCLGHQVPCCDPCATCYCRFFNAFCYC | <u>R</u>K<u>L</u>GTTTNPCS<u>R</u>T | SEQ ID No. 9 |
| Mouse | SP<u>RR</u> | CVRLHESCLGQQVPCCDPCATCYCRFFNAFCYC | <u>R</u>K<u>L</u>GTATNLCS<u>R</u>T | SEQ ID No. 10 |
| Rat | SP<u>RR</u> | CVRLHESCLGQQVPCCDLCATCYCRFFNTFCYC | <u>R</u>K<u>L</u>GTGTTNLCS<u>R</u>P | SEQ ID No. 11 |
| Pig | SP<u>RR</u> | CVRLHESCLGHQVPCCDPCATCYCRFFNAFCYC | <u>R</u>K<u>L</u>GTATNPCS<u>R</u>T | SEQ ID No. 12 |
| Sheep | SP<u>RR</u> | CVRLHESCLGHQVPCCDPCATCYCRFFNAFCYC | <u>R</u>K<u>L</u>GTTT | SEQ ID No. 13 |
| Designed AgRP Sequences | | | | |
| AgRP(83-120) | SS<u>RR</u> | CVRLHESCLGQQVPCCDPAATCYCRFFNAFCYC | <u>R</u> | SEQ ID No. 1 |
| AgRP(87-132) | | CVRLHESCLGQQVPCCDPCATCYCRFFNAFCYC | <u>R</u>K<u>L</u>GTAMNPCS<u>R</u>T | SEQ ID No. 2 |
| AgRP(87-120) | | CVRLHESCLGQQVPCCDPAATCYCRFFNAFCYC | <u>R</u> | SEQ ID No. 3 |
| AgRP-2Q | SS<u>RR</u> | CVRLHESCLGQQVPCCDPCATCYCRFFNAFCYC | <u>R</u>QLGTAMNPCSQT | SEQ ID No. 4 |
| AgRP-4Q | SSQQ | CVRLHESCLGQQVPCCDPCATCYCRFFNAFCYC | <u>R</u>QLGTAMNPCSQT | SEQ ID No. 5 |
| AgRP-2K | SS<u>RR</u> | CVRLHESCLGQQVPCCDPCATCYCRFFNAFCYC | <u>R</u>K<u>L</u><u>K</u>T<u>K</u>MNPCS<u>R</u>T | SEQ ID No. 6 |
| AgRP-4K | <u>KKRR</u> | CVRLHESCLGQQVPCCDPCATCYCRFFNAFCYC | <u>R</u>K<u>L</u><u>K</u>T<u>K</u>MNPCS<u>R</u>T | SEQ ID No. 7 |

Basic residues in the N-terminal segment and C-terminal loop are shown underlined (or in blue in color version).

ICV injections were administered to Long Evans rats fitted with cannulas in the third ventricle. Proteins were delivered as a single 1.0 nmol dose in 1.0 µL of solution. Feeding and weight were monitored in most cases until consumption returned to baseline values. Results for wild type AgRP(83-132) and the three truncated variants are shown in FIG. 2a. All initially stimulate feeding, as seen in the responses after one day. AgRP(83-132) is the most potent, stimulating feeding nearly 80% over that of control, while mini-AgRP is the least potent. Interestingly, AgRP(83-120) is essentially equipotent to wild type. At three or four days after injection, enhanced feeding relative to control diminishes. Animals dosed with the three truncated variants are almost back to baseline. In contrast, those treated with AgRP(83-132) are still consuming feed about 30% over control.

The data in FIG. 2a suggest that the four residue non-ICK segment preceding the ICK core is required for rapidly stimulating feeding, whereas both non-ICK segments are needed for long term effects. The significant number of basic, positively charged residues carried in the non-ICK segments motivated the inventors to examine the relationship between 24 hour feeding and charge per residue (total protein charge divided by the number of amino acids) for the four proteins, as shown in FIG. 2b. Interestingly, there is an approximate linear relationship, with a near four-fold increase in feeding from a doubling of the protein charge density.

Charge Modified AgRP Variants

Figure 3:
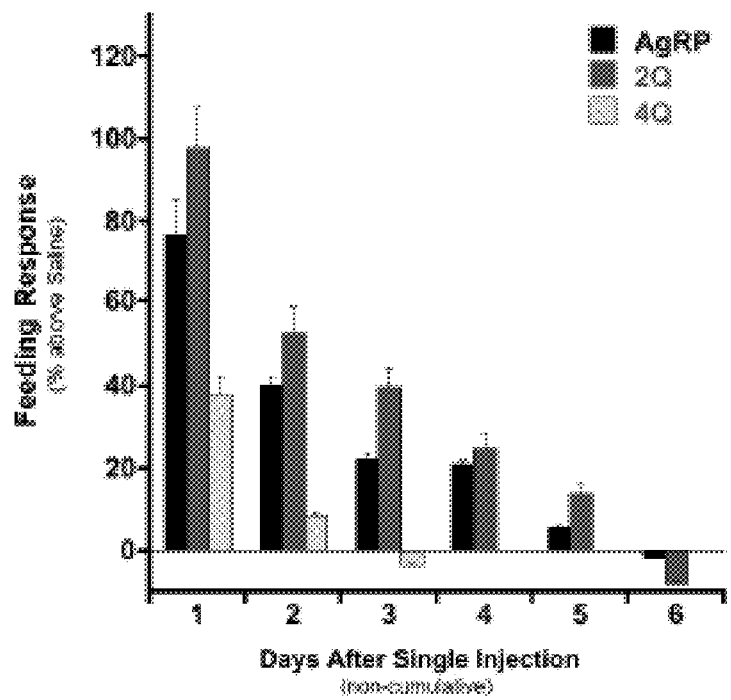
FIG. 3. Effect of a single third cerebral ventricular injection of 1.0 nmol AgRP construct on male Long-Evans rats. (A and B) Non-cumulative percent increase of feeding response compared to saline of AgRP proteins with modified charges. (C) Relationship between 24 hr feeding and net charge density for all AgRP constructs. (D) 5-Day change in body mass and (E) trend in net peptide charge and 5-day change in body mass. ✦ $P<0.001$, ‡ $P<0.01$, and * $P<0.05$ vs saline.
Figure 3:
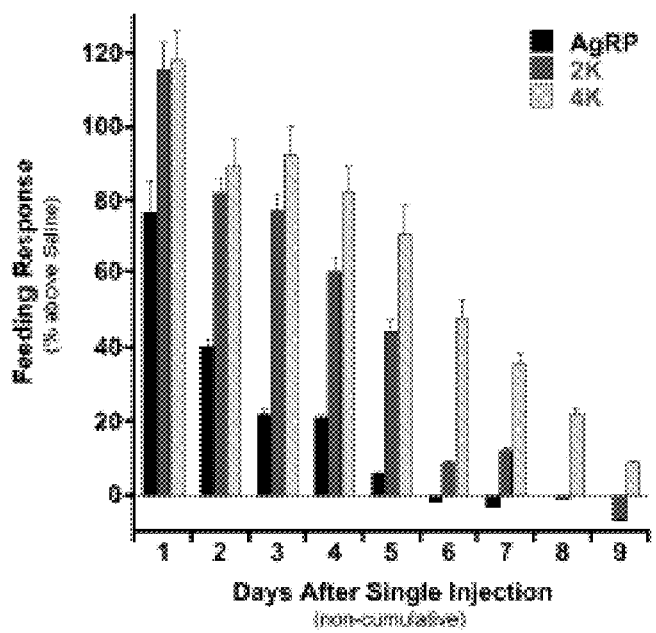
Figure 3:
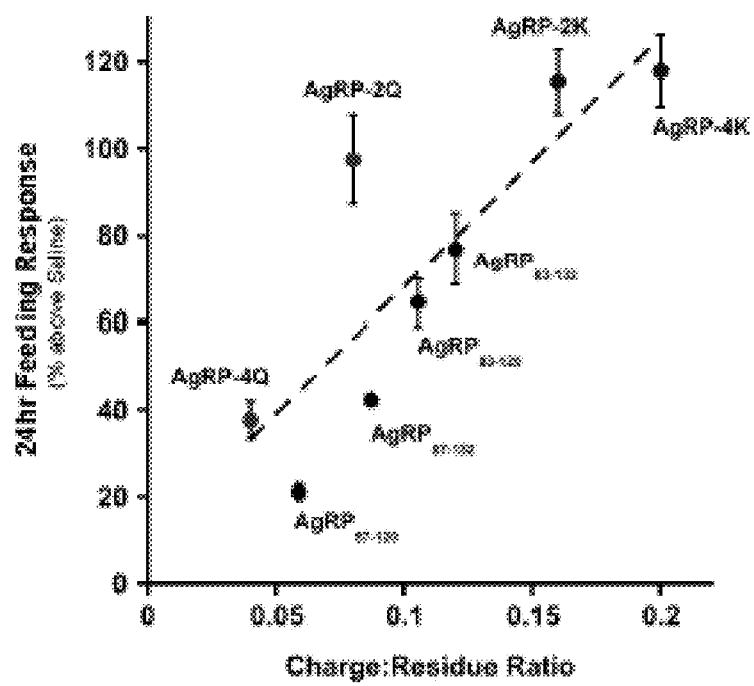
Figure 3:
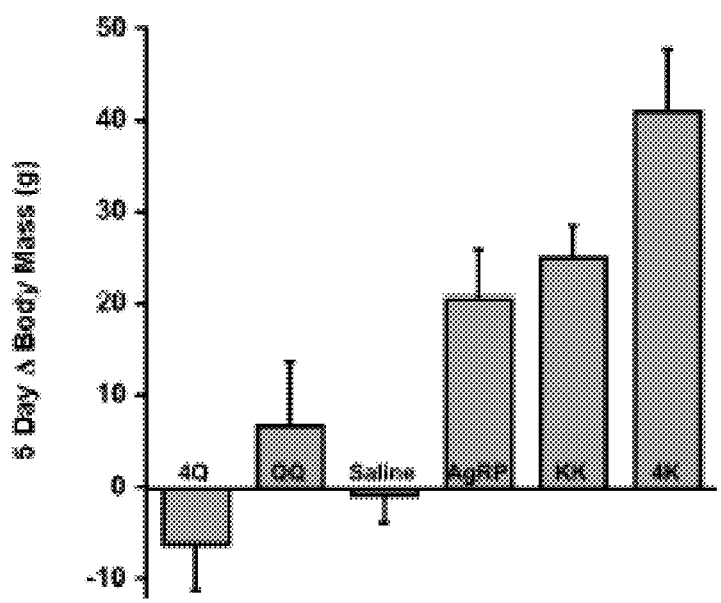
Figure 3:
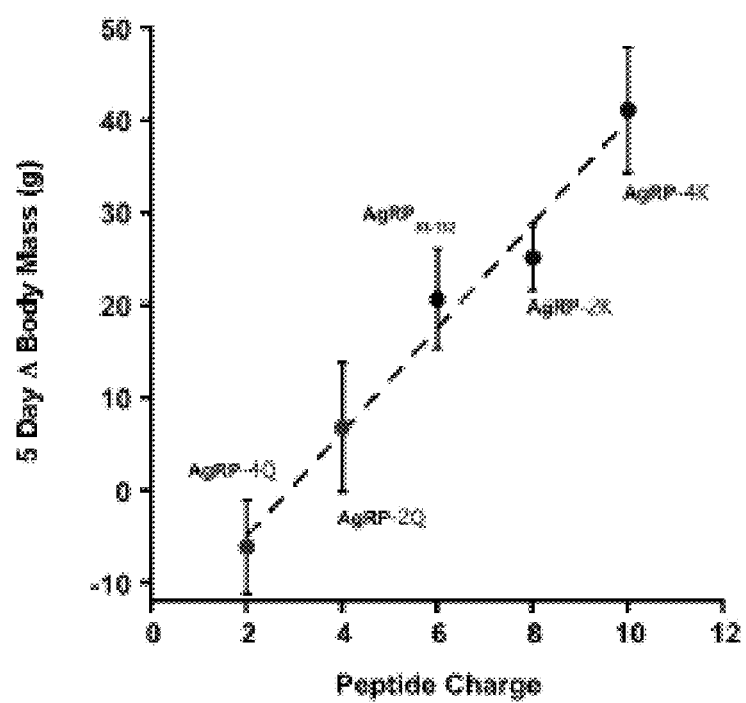

The inventors further tested the role of charge with a series of mutations in full AgRP(83-132). To eliminate positive charges, the inventors replaced Arg or Lys with Gln, which retains local side chain steric features and preserves solubility in aqueous solution (Table 1). AgRP-2Q lacks two charges in the C-terminal loop, whereas AgRP-4Q lacks charges in both the N-terminal segment and the C-terminal loop. Feeding behavior after ICV injection is shown in FIG. 3a. Both AgRP and AgRP-2Q greatly stimulate feeding in the first 24 hours. Consistent with the data of FIG. 2, basic residues within the C-terminal loop are not important for the initial feeding response. Interestingly, AgRP-2Q is somewhat more potent than wild type in both short and long term feeding responses. In contrast, AgRP-4Q gives a weak 24 hour response and returns to baseline after the second day. AgRP-4Q elicits responses similar to that of AgRP(87-120) demonstrating that elimination of the non-ICK segments, or simply the basic residues within these segments, is sufficient to reduce both short and long term potency.

Figure 4:
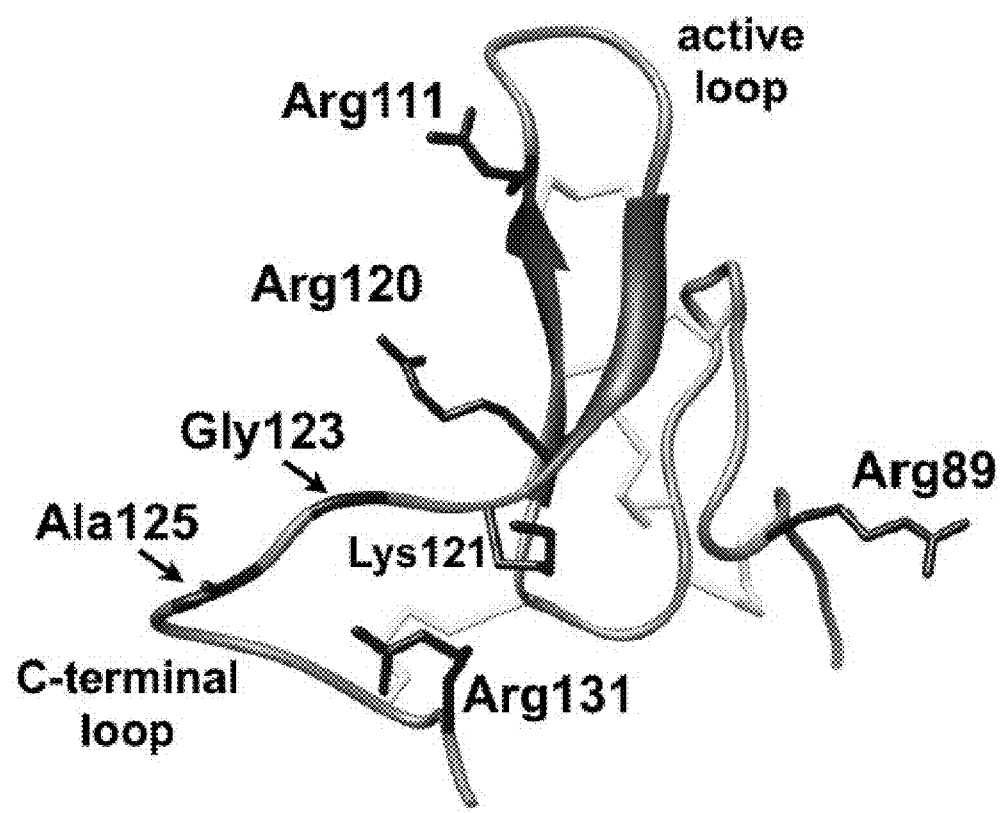
FIG. 4. Cluster of basic residues (blue) in AgRP(83-132) from the active and C-terminal loops. AgRP-2K was developed by mutation of Gly123 and Ala125 (arrows) to Arg. Basic residues are in the N-terminal segment (Ser-Ser-Arg-Arg) are not shown.

To further test the relationship between positive charge and feeding stimulation, the inventors developed AgRP analogues with additional Lys residues. Inspection of the wild type AgRP(83-132) three dimensional structure reveals a cluster of basic residues extending from the active loop (FIG. 1) to the end of the C-terminal loop, as shown in FIG. 4. The inventors reasoned that this conserved spatial arrangement could play a part in the feeding enhancement observed for AgRP(83-132) relative to AgRP(83-120). Consequently, the inventors considered positions contiguous with this cluster. Among the possible positions, the inventors chose to mutate Gly123 and Ala125 since these amino acids lack side chain functional groups and are therefore unlikely to play a structural role. The resulting double mutant is referred to as AgRP-2K. The inventors additionally replaced the two Ser residues in the N-terminal segment with Lys, giving the AgRP-4K analog.

The results following ICV injection of AgRP-2K and AgRP-4K are striking, as shown in FIG. 3b. AgRP-2K elicits an approximate 50% increase in food uptake relative to wild type AgRP in the first 24 hours, and continues to stimulate feeding out to six or seven days. The initial response from AgRP-4K is similar to that of AgRP-2K, but here the animals display elevated feeding beyond nine days, at which point the experiments were halted. The relationship between 24 hour feeding and charge density in the Gln and Lys mutants is displayed in FIG. 3c and supports linear behavior observed for the truncated AgRP variants. Finally, the inventors examined the change in body mass five days after injection, as shown in FIG. 4d. The results parallel the relationship observed between charge and 24 hour feeding (FIG. 3e), with AgRP-4Q giving a slight decrease in body mass, and AgRP-4K giving by far the greatest increase. Moreover, AgRP-4K leads to an increase in body mass that is approximately double that observed for wild type AgRP(83-132).

Mc3R and Mc4R Pharmacology

Figure 5:
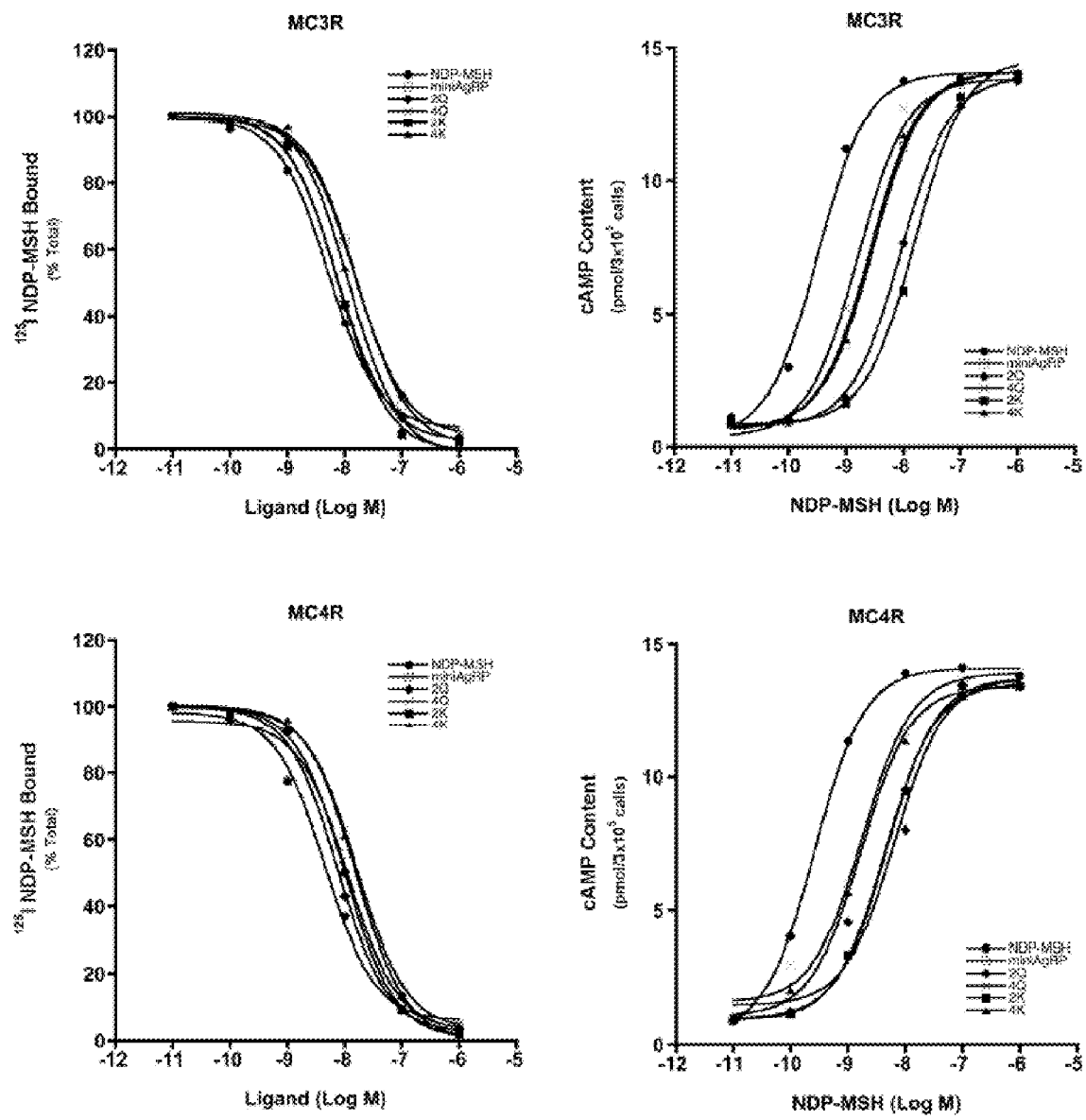
FIG. 5. Pharmacology of novel AgRP constructs at MC3r and MC4r. (A & C) Displacement of $^{125}$I-NDP-MSH; (C & D) cAMP production from increasing NDP-MSH concentrations in the presence of 0.10 µM AgRP proteins.

The inventors used both displacement and activity assays to evaluate the influence of truncation or charge alteration on receptor pharmacology. Measurements were performed on HEK293 cells expressing the desired receptor subtype. FIG. 5 shows $^{125}$I-NDP-MSH displacement for all variants at Mc3R and Mc4R, with $K_i$ values reported in Table 2. Variation is limited from 4.5 to 16 nM at Mc3R, and from 7.6 to 16 nM at Mc4R. The variants that give the strongest feeding response fall in the middle of the $K_i$ range and, in general, do not suggest any relationship between dissociation constant and short term or long term consumption. Each variant was further evaluated for its ability to suppress NDP-MSH stimulated cAMP production. Antagonists give a rightward shift in the response curve. The results are shown in FIG. 5, and $EC_{50}$ values in Table 2. The $EC_{50}$ values also exhibit limited variation, although greater than observed for the displacement studies, and range from 1.6 to 16 nM at Mc3R, and 1.7 to 17 nM at Mc4R. Interestingly, the lowest $EC_{50}$ values at both receptors are observed for the AgRP-4Q and AgRP-4K variants, which elicit opposite feeding responses.

TABLE 2

Ligand Displacement and EC50 Values

| Peptide | MC3R | | MC4R | |
| --- | --- | --- | --- | --- |
| | $K_i$ (nM) | $EC_{50}$ (nM) | $K_i$ (nM) | $EC_{50}$ (nM) |
| AgRP(83-132) | ND | ND | 11 ± 0.7[d] | ND |
| AgRP(87-132) | 5.2 ± 0.7[a] | 8.9 ± 0.2[c] | 11 ± 1[a] | 17 ± 3[b] |
| AgRP(83-120) | 16.5 ± 0.4 | 2.96 ± 0.4 | 11.4 ± 4 | 4.92 ± 1.3 |
| AgRP(87-120) | 7.5 ± 0.5[a] | 5.5 ± 0.2 | 6.1 ± 0.5[a] | 13 ± 3[b] |
| AgRP-2Q | 7.56 ± 1.3 | 9.22 ± 1.4 | 7.56 ± 0.3 | 6.66 ± 2.1 |
| AgRP-4Q | 15.6 ± 0.3 | 1.62 ± 0.3 | 16.2 ± 0.7 | 1.8 ± 0.5 |
| AgRP-2K | 7.84 ± 0.5 | 16.1 ± 1.6 | 9.99 ± 3.7 | 4.54 ± 1.3 |
| AgRP-4K | 11.91 ± 4 | 2.66 ± 0.3 | 15.65 ± 1.4 | 1.72 ± 0.4 |

ND, Not Determined
[a]Data adapted from Jackson et al. (Jackson et al., 2002)
[b]Data adapted from Patel et al. (Patel et al., 2010)
[c]Data adapted from Wilczynski et al. (Wilczynski et al., 2004)
[d]Data adapted from Creemers et al. (Creemers et al., 2006)

DISCUSSION

The findings above identify an unanticipated and dramatic functional role for the AgRP polypeptide segments outside of the ICK core domain. The data provide unexpectedly superior results when the polypeptides of the invention are used as an appetite stimulant. Comparison of wild type AgRP to a mini-AgRP, composed of only the ICK core, shows that the Ser-Ser-Arg-Arg N-terminal extension and the C-terminal loop greatly enhance both the initial and long-term feeding responses. Of these two non-ICK segments, the N-terminal extension is more important, especially for the initial feeding response, but both play a role in sustaining feeding levels above baseline. By evaluation of designed AgRP mutants, the inventors further showed that positive charge conferred by basic residues in these segments is responsible for the observed in vivo responses. Inclusion of additional charges beyond those found in wild type results in a protein that generates a profound feeding response that lasts almost twice as long as that induced by the wild type AgRP.

It is unlikely that these results arise from modulation in receptor binding affinity, as the measured dissociation constants and cAMP activities at Mc3R and Mc4R exhibit little variation and no correlation with feeding behavior.

Examination of mammalian AgRP sequences reveals some variation in the two non-ICK segments, but always at positions that do not carry positive charge (Table 1) (Jackson et al., 2006; McNulty et al., 2001). The basic Lys and Arg residues are completely conserved, and acidic residues are never found at sites that do exhibit variation. It is unlikely that these segments play a structural role. Structure determination by NMR, performed by our lab, found that the C-terminal loop is flexible and points away from the ICK core containing four of the five disulfide bonds (McNulty et al., 2001). Moreover, the mini-AgRP construct folds cooperatively with stability that is indistinguishable from AgRP(83-132) (Jackson et al., 2002). Interestingly, the mini-AgRP core domain is so stable that it is now being used as a scaffold in protein design (Jiang et al., 2010; Silverman et al., 2011; Silverman et al., 2009).

There is also no evidence that these segments are required for in vivo processing to produce mature AgRP(83-132). As noted in the previously, AgRP is produced as a pro-protein that undergoes processing by the serine endoprotease PC ⅓. AgRP residues 79-82 (Arg-Glu-Pro-Arg) follow the P4-P1 consensus sequence targeting cleavage to the Arg82-Ser83 peptide bond. Alternate cleavage sights are not observed; the processed form of the protein is found exclusively as AgRP (83-132) (Breen et al., 2005). Moreover, PC ⅓ is tolerant of sequence variations at the P1'-P4' sites (Ser-Ser-Arg-Arg in AgRP) SEQ ID 14 following the cleavage point, thus suggesting a distinct role for the conserved Arg85-Arg86 residues (Duckert et al., 2004).

Among the known collection of natural and synthetic orexigenic peptides, AgRP exhibits the greatest overall potency. For example, a single 1.0 nM dose of neuropeptide Y (NPY) rapidly stimulates feeding beyond that of an equivalent dose of AgRP, but its effects quickly dissipate and feeding returns to baseline after 24 hours (Flynn et al., 1999; Hagan et al., 2000). The synthetic cyclic hexapeptide SHU9119 gives a long-term response similar to AgRP, but requires higher minimal doses for activation (Joppa et al., 2005).

Because of its unique behavior, AgRP is considered to be an important lead in the development of drugs for treating cachexia (Marks et al., 2001). Cachexia is a state of negative energy balance that often arises with cancer, AIDS, kidney failure and leads to malnutrition and loss of body mass (Grossberg et al., 2010; Krasnow and Marks, 2010). Maintaining positive energy balance, on the other hand, correlates strongly with the outcome of cancer patients undergoing radiation or chemotherapy. Consistent with the role of the melanocortin system in maintaining energy balance, animal models driven to cachexia by tumors or administration of lipopolysaccharide (LPS) resume normal feeding and body weight from the administration of Mc4R antagonists, including AgRP. It is therefore noteworthy that our findings here identify new features that enhance AgRP function and prolong efficacy by nearly a factor of two.

It is clear from the disclosed experiments that AgRP's basic residues, outside of the ICK core McR recognition domain, play a central role in modulating short- and long-term AgRP function. Although the direct mechanism linking positive charge to AgRP function is not clear, the inventors note three possibilities. First, the basic residues may increase AgRP diffusibility thereby moving the protein more efficiently from the ventricle to the hypothalamus. Second, they may slow degradation or facilitate interactions with accessory molecules proximal to the melanocortin receptors. For example, negatively charged syndecans, cell surface proteoglycans, are implicated in McR regulation. New experiments show that AgRP localization in the paraventricular nucleus is reduced in syndecan knockout mice, suggesting that syndecans are required for concentrating AgRP at postsynaptic membranes. Finally, the basic residues may facilitate signaling through a non-McR pathway. In support of this mechanism, injection of the synthetic agonist MTII, following AgRP administration, transiently reduces feeding, which then returns to the level consistent with AgRP dose. Moreover, loss of feeding regulation, resulting from selective ablation of AgRP neurons, is not reversed by increased ASIP levels.

In summary, the inventors have demonstrated a clear functional role for AgRP's conserved non-ICK segments. The basic, positively charged residues are vital for AgRP stimulated long-term feeding. Moreover, AgRP may be engineered to have variable long-term feeding profiles. It is very likely that the principles identified here will be helpful in pharmaceutical design for treating cachexia and perhaps other conditions associated with improper energy balance and hunger and feeding control such as anorexia and other disorders.

The invention claimed is:

1. An engineered polypeptide comprising a non-naturally occurring AgRP analog with increased positive charge compared to the wild type AgRP polypeptide, wherein the polypeptide is engineered to include one or more amino acid alterations within one or both of the N-terminal extension and the C-terminal loop, wherein the polypeptide is engineered to include amino acid alterations in the Ser-Ser-Arg-Arg N-terminal extension, and wherein the Ser-Ser-Arg-Arg N-terminal extension is altered to provide additional basic, positively charged amino acid residues beyond those found in wild type AgRP.

2. An engineered polypeptide comprising a non-naturally occurring AgRP analog with increased positive charge compared to the wild type AgRP polypeptide, wherein the polypeptide is engineered to include one or more amino acid alterations within one or both of the N-terminal extension and the C-terminal loop, and wherein the polypeptide is engineered to include amino acid alterations in the 13 residue C-terminal loop to provide additional basic, positively charged amino acid residues beyond those found in wild type AgRP.

3. An engineered polypeptide comprising a non-naturally occurring AgRP analog with increased positive charge compared to the wild type AgRP polypeptide, wherein the AgRP analog comprises a non-naturally occurring amino acid sequence having 100% polypeptide sequence identity to a polypeptide sequence selected from the group consisting of:

SEQ ID No. 1, SEQ ID No. 4, SEQ ID No. 5, SEQ ID No. 6, and SEQ ID No. 7.

4. A method for increasing appetite or investigating the physiological role of AgRPs, the method comprising administering to a subject the engineered polypeptide of claim 1, whereby the engineered polypeptide stimulates appetite and results in enhanced feeding over a 24 hour period that is measurably at least double that obtained when unaltered AgRP is introduced into the CNS of a mammal.

5. The method of claim 4 further used for investigating or treating cachexia.

6. The method of claim 5 further used for investigating or treating cachexia associated with a disease selected from the group consisting of cancer, AIDS, and kidney failure.

7. The method of claim 4 comprising administering to a subject AgRP-4K (SEQ ID No.7) resulting in enhanced feeding.

8. An engineered polypeptide comprising a non-naturally occurring AgRP analog with increased positive charge compared to the wild type AgRP polypeptide, wherein the polypeptide is engineered to include amino acid alterations within the N-terminal extension and the C-terminal loop, and wherein the non-naturally occurring AgRP analog comprises deletions of both the four residue segment before the ICK domain, and the C-terminal loop.

* * * * *

SEQUENCE LISTING

```
<160> NUMBER OF SEQ ID NOS: 14

<210> SEQ ID NO 1
<211> LENGTH: 38
<212> TYPE: PRT
<213> ORGANISM: Artificial Sequence
<220> FEATURE:
<223> OTHER INFORMATION: AgRP(83-120): peptide designed as a truncation
      of human Agouti-Related Protein.

<400> SEQUENCE: 1

Ser Ser Arg Arg Cys Val Arg Leu His Glu Ser Cys Leu Gly Gln Gln
1               5                   10                  15

Val Pro Cys Cys Asp Pro Ala Ala Thr Cys Tyr Cys Arg Phe Phe Asn
            20                  25                  30

Ala Phe Cys Tyr Cys Arg
        35

<210> SEQ ID NO 2
<211> LENGTH: 46
<212> TYPE: PRT
<213> ORGANISM: Artificial Sequence
<220> FEATURE:
<223> OTHER INFORMATION: AgRP(87-132): peptide designed as a truncation
      of human Agouti-Related Protein.

<400> SEQUENCE: 2

Cys Val Arg Leu His Glu Ser Cys Leu Gly Gln Gln Val Pro Cys Cys
1               5                   10                  15

Asp Pro Cys Ala Thr Cys Tyr Cys Arg Phe Phe Asn Ala Phe Cys Tyr
            20                  25                  30

Cys Arg Lys Leu Gly Thr Ala Met Asn Pro Cys Ser Arg Thr
        35                  40                  45

<210> SEQ ID NO 3
<211> LENGTH: 34
<212> TYPE: PRT
<213> ORGANISM: Artificial Sequence
<220> FEATURE:
<223> OTHER INFORMATION: AgRP(87-120): peptide designed as a truncation
      of Human Agouti-Related Protein.

<400> SEQUENCE: 3

Cys Val Arg Leu His Glu Ser Cys Leu Gly Gln Gln Val Pro Cys Cys
1               5                   10                  15

Asp Pro Ala Ala Thr Cys Tyr Cys Arg Phe Phe Asn Ala Phe Cys Tyr
            20                  25                  30

Cys Arg
```

-continued

```
<210> SEQ ID NO 4
<211> LENGTH: 50
<212> TYPE: PRT
<213> ORGANISM: Artificial Sequence
<220> FEATURE:
<223> OTHER INFORMATION: AgRP-2Q: peptide designed to eliminate positive
      charges from AgRP(83-132).

<400> SEQUENCE: 4

Ser Ser Arg Arg Cys Val Arg Leu His Glu Ser Cys Leu Gly Gln Gln
1               5                   10                  15

Val Pro Cys Cys Asp Pro Cys Ala Thr Cys Tyr Cys Arg Phe Phe Asn
                20                  25                  30

Ala Phe Cys Tyr Cys Arg Gln Leu Gly Thr Ala Met Asn Pro Cys Ser
            35                  40                  45

Gln Thr
    50

<210> SEQ ID NO 5
<211> LENGTH: 50
<212> TYPE: PRT
<213> ORGANISM: Artificial Sequence
<220> FEATURE:
<223> OTHER INFORMATION: AgRP-4Q: peptide designed to eliminate positive
      charges from AgRP(83-132).

<400> SEQUENCE: 5

Ser Ser Gln Gln Cys Val Arg Leu His Glu Ser Cys Leu Gly Gln Gln
1               5                   10                  15

Val Pro Cys Cys Asp Pro Cys Ala Thr Cys Tyr Cys Arg Phe Phe Asn
                20                  25                  30

Ala Phe Cys Tyr Cys Arg Gln Leu Gly Thr Ala Met Asn Pro Cys Ser
            35                  40                  45

Gln Thr
    50

<210> SEQ ID NO 6
<211> LENGTH: 50
<212> TYPE: PRT
<213> ORGANISM: Artificial Sequence
<220> FEATURE:
<223> OTHER INFORMATION: AgRP-2K: peptide designed with additional
      Lysine residues in AgRP(83-132).

<400> SEQUENCE: 6

Ser Ser Arg Arg Cys Val Arg Leu His Glu Ser Cys Leu Gly Gln Gln
1               5                   10                  15

Val Pro Cys Cys Asp Pro Cys Ala Thr Cys Tyr Cys Arg Phe Phe Asn
                20                  25                  30

Ala Phe Cys Tyr Cys Arg Lys Leu Lys Thr Lys Met Asn Pro Cys Ser
            35                  40                  45

Arg Thr
    50

<210> SEQ ID NO 7
<211> LENGTH: 50
<212> TYPE: PRT
<213> ORGANISM: Artificial Sequence
<220> FEATURE:
<223> OTHER INFORMATION: AgRP-4K: peptide designed with additional
      Lysine residues in AgRP(83-132).

<400> SEQUENCE: 7
```

```
Lys Lys Arg Arg Cys Val Arg Leu His Glu Ser Cys Leu Gly Gln Gln
1               5                   10                  15

Val Pro Cys Cys Asp Pro Cys Ala Thr Cys Tyr Cys Arg Phe Phe Asn
                20                  25                  30

Ala Phe Cys Tyr Cys Arg Lys Leu Lys Thr Lys Met Asn Pro Cys Ser
            35                  40                  45

Arg Thr
    50

<210> SEQ ID NO 8
<211> LENGTH: 50
<212> TYPE: PRT
<213> ORGANISM: Homo sapiens

<400> SEQUENCE: 8

Ser Ser Arg Arg Cys Val Arg Leu His Glu Ser Cys Leu Gly Gln Gln
1               5                   10                  15

Val Pro Cys Cys Asp Pro Cys Ala Thr Cys Tyr Cys Arg Phe Phe Asn
                20                  25                  30

Ala Phe Cys Tyr Cys Arg Lys Leu Gly Thr Ala Met Asn Pro Cys Ser
            35                  40                  45

Arg Thr
    50

<210> SEQ ID NO 9
<211> LENGTH: 50
<212> TYPE: PRT
<213> ORGANISM: Bos taurus

<400> SEQUENCE: 9

Ser Pro Arg Arg Cys Val Arg Leu His Glu Ser Cys Leu Gly His Gln
1               5                   10                  15

Val Pro Cys Cys Asp Pro Cys Ala Thr Cys Tyr Cys Arg Phe Phe Asn
                20                  25                  30

Ala Phe Cys Tyr Cys Arg Lys Leu Gly Thr Thr Thr Asn Pro Cys Ser
            35                  40                  45

Arg Thr
    50

<210> SEQ ID NO 10
<211> LENGTH: 50
<212> TYPE: PRT
<213> ORGANISM: Mus musculus

<400> SEQUENCE: 10

Ser Pro Arg Arg Cys Val Arg Leu His Glu Ser Cys Leu Gly Gln Gln
1               5                   10                  15

Val Pro Cys Cys Asp Pro Cys Ala Thr Cys Tyr Cys Arg Phe Phe Asn
                20                  25                  30

Ala Phe Cys Tyr Cys Arg Lys Leu Gly Thr Ala Thr Asn Leu Cys Ser
            35                  40                  45

Arg Thr
    50

<210> SEQ ID NO 11
<211> LENGTH: 51
<212> TYPE: PRT
<213> ORGANISM: Rattus norvegicus

<400> SEQUENCE: 11
```

```
Ser Pro Arg Arg Cys Val Arg Leu His Glu Ser Cys Leu Gly Gln Gln
1               5                   10                  15

Val Pro Cys Cys Asp Leu Cys Ala Thr Cys Tyr Cys Arg Phe Phe Asn
                20                  25                  30

Thr Phe Cys Tyr Cys Arg Lys Leu Gly Thr Gly Thr Thr Asn Leu Cys
            35                  40                  45

Ser Arg Pro
    50

<210> SEQ ID NO 12
<211> LENGTH: 50
<212> TYPE: PRT
<213> ORGANISM: Sus scrofa

<400> SEQUENCE: 12

Ser Pro Arg Arg Cys Val Arg Leu His Glu Ser Cys Leu Gly His Gln
1               5                   10                  15

Val Pro Cys Cys Asp Pro Cys Ala Thr Cys Tyr Cys Arg Phe Phe Asn
                20                  25                  30

Ala Phe Cys Tyr Cys Arg Lys Leu Gly Thr Ala Thr Asn Pro Cys Ser
            35                  40                  45

Arg Thr
    50

<210> SEQ ID NO 13
<211> LENGTH: 44
<212> TYPE: PRT
<213> ORGANISM: Ovis aries

<400> SEQUENCE: 13

Ser Pro Arg Arg Cys Val Arg Leu His Glu Ser Cys Leu Gly His Gln
1               5                   10                  15

Val Pro Cys Cys Asp Pro Cys Ala Thr Cys Tyr Cys Arg Phe Phe Asn
                20                  25                  30

Ala Phe Cys Tyr Cys Arg Lys Leu Gly Thr Thr Thr
            35                  40

<210> SEQ ID NO 14
<211> LENGTH: 4
<212> TYPE: PRT
<213> ORGANISM: Homo sapiens

<400> SEQUENCE: 14

Arg Glu Pro Arg
1
```